United States Patent [19]
Lorentzen

[11] Patent Number: 5,951,546
[45] Date of Patent: Sep. 14, 1999

[54] ELECTROSURGICAL INSTRUMENT FOR TISSUE ABLATION, AN APPARATUS, AND A METHOD FOR PROVIDING A LESION IN DAMAGED AND DISEASED TISSUE FROM A MAMMAL

[76] Inventor: Torben Lorentzen, Ordrupdalvej 11, DK-2920 Charlottenlund, Denmark

[21] Appl. No.: 08/849,675
[22] PCT Filed: Nov. 24, 1995
[86] PCT No.: PCT/DK95/00471
  § 371 Date: Sep. 30, 1997
  § 102(e) Date: Sep. 30, 1997
[87] PCT Pub. No.: WO96/18349
  PCT Pub. Date: Jun. 20, 1996

[30] Foreign Application Priority Data
Dec. 13, 1994 [DK] Denmark .................................. 142494

[51] Int. Cl.⁶ ........................................................ A61B 17/39
[52] U.S. Cl. .................................. 606/41; 606/49; 607/99
[58] Field of Search .................................. 606/41, 45, 46, 606/48, 49, 50; 607/99

[56] References Cited

U.S. PATENT DOCUMENTS

| | | | |
|---|---|---|---|
| 4,532,924 | 8/1985 | Auth et al. | 128/303.17 |
| 4,961,535 | 10/1990 | Kitagawa et al. | 128/788 |
| 5,348,554 | 9/1994 | Imran et al. | 606/41 |
| 5,403,311 | 4/1995 | Abele et al. | 606/49 |
| 5,609,151 | 3/1997 | Mulier et al. | 607/99 |

OTHER PUBLICATIONS

Livraghi et al. (1995) "Saline–enhanced RF Tissue Ablation in the Treatment of Liver Metastases", *Radiology*, 197(P): 140 (abstr).

McGaha et al. (1995) "Percutaneous Ultrasound–guided Radiofrequency Electrocautery Ablationof Prostate Tissue in Dogs", *Acad Radiol*, vol. 2, No. 1:pp. 61–65.

Goldberg et al. (1995) "Tissue Ablation with Radiofrequency Using Multiprobe Arrays", *Acad Radiol*, vol. 2: pp. 399–404.

Goldberg et al. (1995) "Saline–enhanced RF Ablation: Demonstration of Efficacy and Optimization of Parameter", *Radiology*, 197(P): 140 (Abstr).

Reidenbach (1995) "First Experimental Results with Special Applicators for High–Frequency Interstitial Thermotherapy", *Society Minimally Ivasive Therapy*, 4(Suppl 1):40 (Abstr).

Solbiati et al. (1995) "Percutaneous US–guided RF Tissue Ablation of Liver Metastases: Long–term Follow–up", *Radiology*, 197(P): 199 (abstr).

Organ LW. (1976) "Electrophysiologic Principles of Radiofrequency Lesion Making" *Appl. Neurophysiol*, vol. 39: pp. 69–76.

*Primary Examiner*—Lee Cohen
*Attorney, Agent, or Firm*—Klein & Szekeres, LLP

[57] ABSTRACT

An electrosurgical instrument, an apparatus employing such instrument, and a method for using such instrument and apparatus for tissue ablation, are useful for forming lesions in tissue, whereby tumors, birth marks, or the like may be removed. The electrosurgical instrument has an elongated tubular element with a distal end and a proximal end, whereby a cooling fluid passage is provided within the tubular element for establishing fluid communication between the proximal end and the distal end. An electrical conductor, provided at the proximal end, supplies electrical energy to the distal end. The apparatus includes the electrosurgical instrument, a cooling fluid supply, a counter electrode, and an electrical energy source. In the method of using the instrument and the apparatus, the tubular element is inserted into the tissue, cooling fluid is supplied to the tubular element, and electrical energy is supplied to the tubular element.

15 Claims, 5 Drawing Sheets

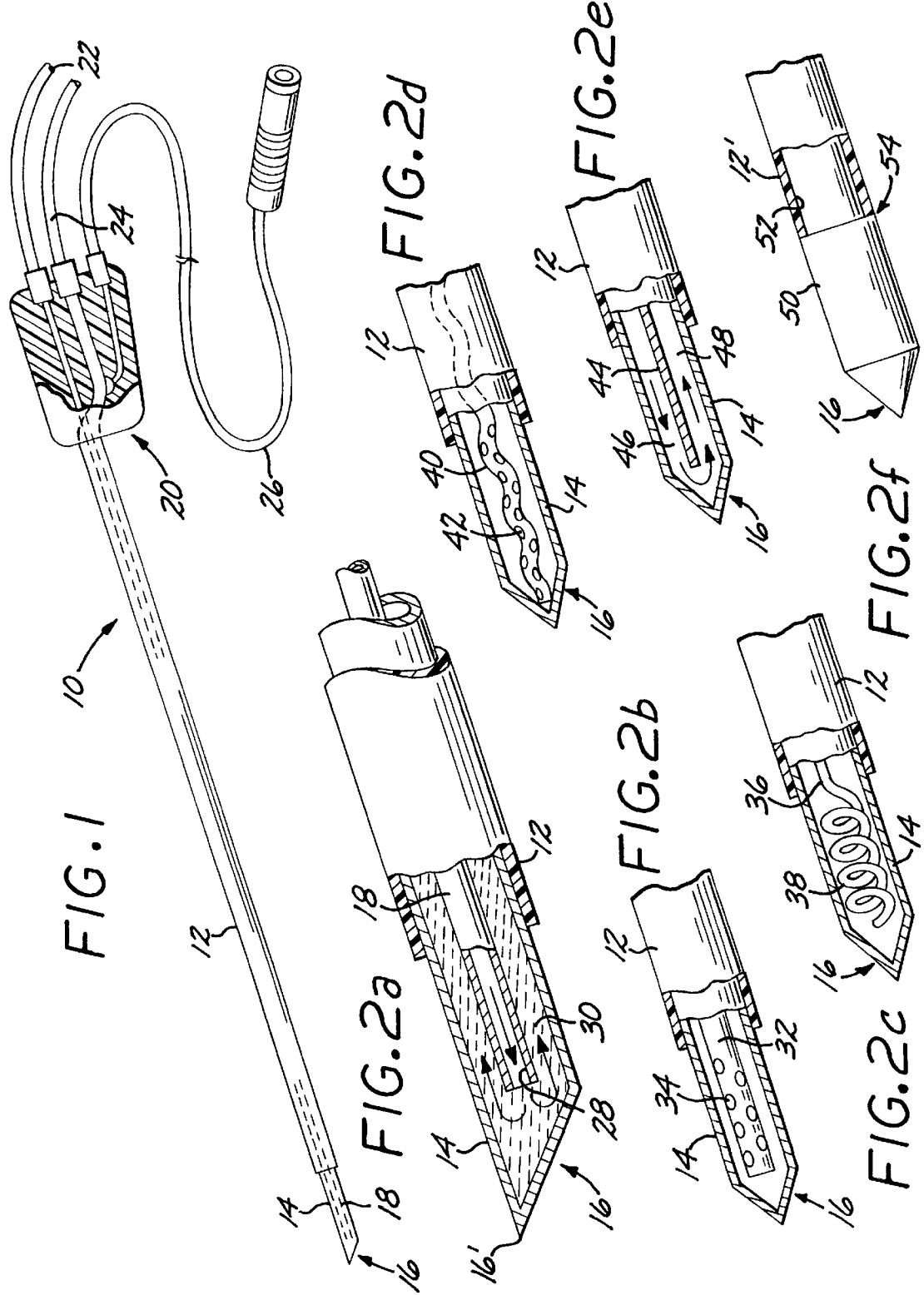

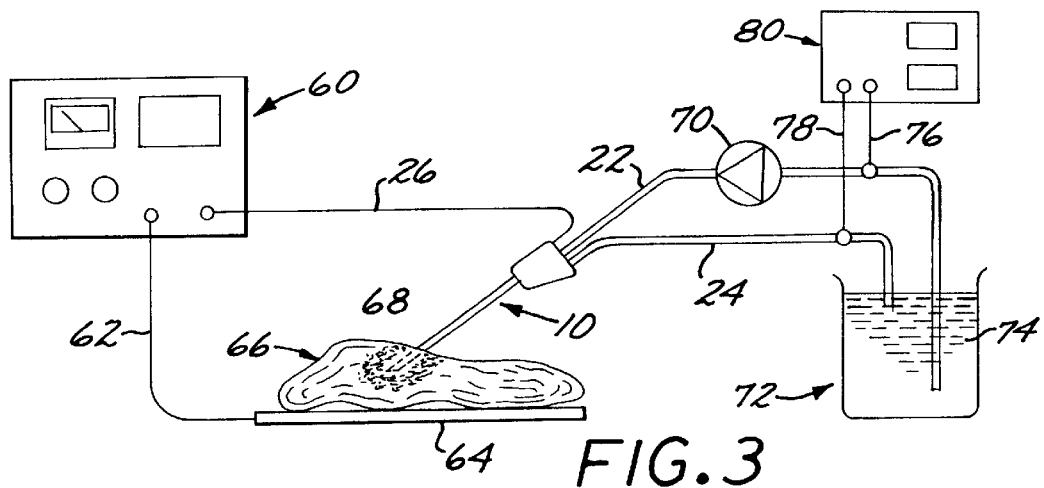
FIG. 3
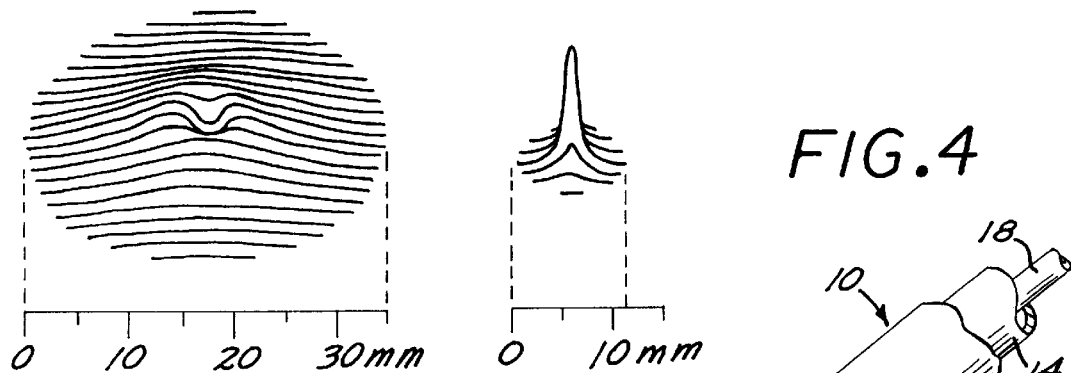
FIG. 4   FIG. 5a   FIG. 5b
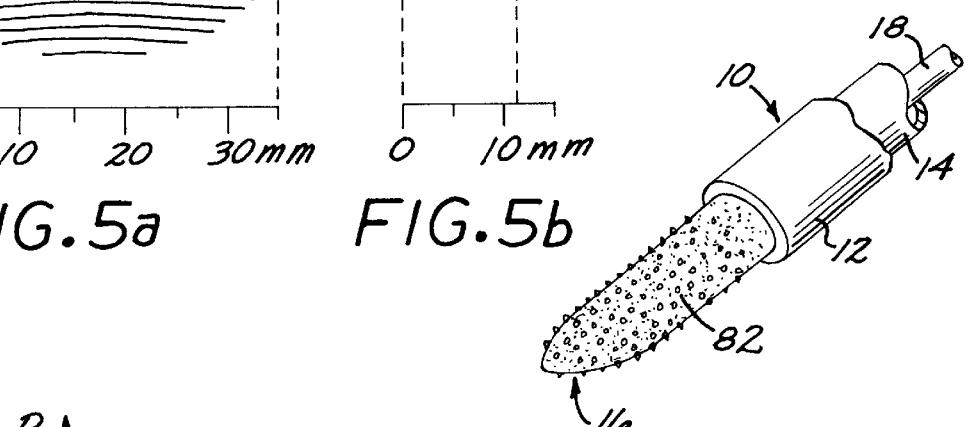
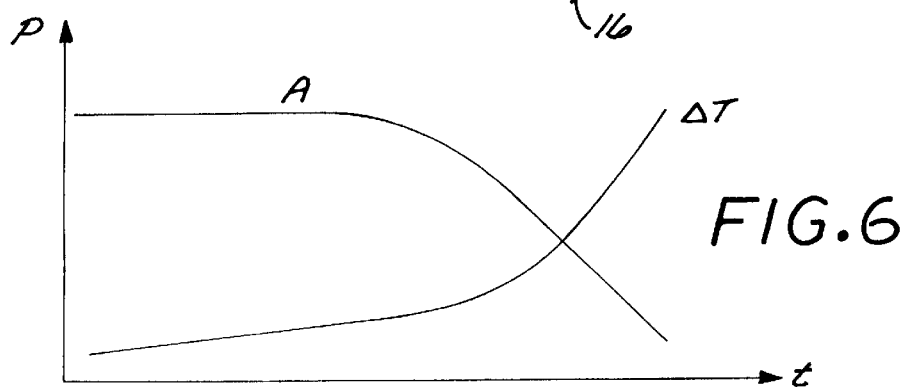
FIG. 6

ELECTROSURGICAL INSTRUMENT FOR TISSUE ABLATION, AN APPARATUS, AND A METHOD FOR PROVIDING A LESION IN DAMAGED AND DISEASED TISSUE FROM A MAMMAL

BACKGROUND OF THE INVENTION

The present invention concerns a novel electrosurgical instrument for tissue ablation, an apparatus for tissue ablation comprising the electrosurgical instrument and a method for providing a lesion in damaged or diseased tissue from a mammal. The present invention is useful for providing a lesion in any biological tissue such as tissue from a mammal. Hereby damaged or diseased tissue such as tumors, birth marks, lipomas, or the like, may be removed.

Radiofrequency (RF) tissue ablation is a well known technique for making thermal lesions around the tip of an electrode due to tissue coagulation caused by resistive heating. The electrode can be applied directly on superficial structures, surgically, endoscopically, laparascopically, or via a transcatheter access—the latter has become a well established treatment for many symptomatic cardiac arrhythmias (see Nath S, Haines D E. Biophysics and pathology of catheter energy deliver systems. Progress in Cardiovascular Disease 1995; 37: 185–204). Furthermore, a needle electrode can be inserted interstitially, mainly guided by imaging. Several studies have evaluated needle electrodes and thermal lesions in different organs such as liver (see McGahan J P, Schneider P, Brock J M, Tesluk H. Treatment of liver tumors by percutaneous radiofrequency electrocautery. Seminars in Interventionel Radiology 1993; 10: 143–149; Rossi S, Fornari F, Buscarini L. Percutaneous ultrasound-guided radiofrequency electrocautery for the treatment of small hepatocellular carcinoma. J Intervent Radiol 1993; 8: 97–103; Solbiati L, Ierace T, Goldberg S N, Livraghi T, Gazelle G S, Rizzatto G. Percutaneous US-guided RF tissue ablation of liver metastases: Long-term follow-up. Radiology 1995; 197(P): 199 (abstr); Livraghi T, Goldberg S N, Lazzaroni S, Meloni F, Monti F, Solbiati L. Saline-enhanced RF tissue ablation in the treatment of liver metastases. Radiology 1995; 197(P): 140 (abstr), prostate (see McGahan J P, Griffey S M, Budenz R W, Brock J M. Percutaneous ultrasound-guided radiofrequency electrocautery ablation of prostate tissue in dogs. Acad Radiol 1995; 2: 61–65, Goldwasser B, Ramon J, Engelberg S. Transurethral needle ablation (TUNA) of the prostate using low level radiofrequency energy: An animal experimental study. Eur Urol 1993; 24: 400–405), and lungs (see Goldberg S N, Gazelle G S, Compton C C, McLoud T C. Radiofrequency tissue ablation in the rabbit lung: Efficacy and complications. Acad Radiol 1995; 2: 776:784). Finally, needle electrodes have been used in neurosurgery for the interruption of pain pathways (see Anzai Y, De Salles A F, Black K L et al: Stereotactic and interventional MRI, in De Salles A F and Goetsch S J (eds): Stereotactic Surgery and Radiosurgery. Madison, Medical Physics Publishing, 1993: 47–60).

The electrophysiologic and thermodynamic conditions in monopolar RF tissue ablation have been described by Organ (see Organ LW. Electrophysiologic principles of radiofrequency lesion making. Appl Neurophysiol 1976; 39:69–76) and Nath et al (see Nath S, Haines D E. Biophysics and pathology of catheter energy deliver systems. Progress in Cardiovascular Disease 1995; 37: 185–204; Nath S, Dimarco J P, Haines DE. Basic aspects of radiofrequency catheter ablation. J Cardiovasc Electrophysiol 1994; 5: 863–876): An RF lesion is the result of tissue destruction due to resistive heating in the tissue that surrounds the uninsulated part of the electrode. Resistive heating is proportional to the square of the current density, the latter being inversely proportional to the square of the distance from the ablation electrode. Therefore, resistive heating decreases from the ablation electrode with the distance to the fourth power. In other words, significant resistive heating only occurs within a narrow rim (few mm) of tissue in direct contact with the ablation electrode. Deeper tissue heating occurs as a result of passive heat conduction from that rim.

A general problem in RF tissue ablation is limitation in lesion size. An increased generator power (Watt) and/or exposure time results in an increased amount of delivered energy (Joule) around the electrode with a resulting increased lesion size. However, at high temperatures (>100° C.) at the electrode-tissue interface the impedance increases significantly because of desiccation followed by charring around the electrode tip. This leads to an abrupt fall in lesion current (and delivered effect) and no further energy is delivered around the electrode, and no further tissue heating occurs. Lesion size will therefore have an upper limit (see Nath S, Haines DE. Biophysics and pathology of catheter energy deliver systems. Progress in Cardiovascular Disease 1995; 37: 185–204; Organ LW. Electrophysiologic principles of radiofrequency lesion making. Appl Neurophysiol 1976; 39:69–76; Nath S, Dimarco J P, Haines D E. Basic aspects of radiofrequency catheter ablation. J Cardiovasc Electrophysiol 1994; 5: 863–876). Thus, it has been difficult to achieve a sufficient coagulation depth, i.e. a sufficient transverse diameter of the lesion. A maximum transverse diameter in the range of 10–15 mm is typically reported, (see McGahan J P, Schneider P, Brock J M, Tesluk H. Treatment of liver tumors by percutaneous radiofrequency electrocautery. Seminars in Interventionel Radiology 1993; 10: 143–149; Rossi S, Fornari F, Buscarini L. Percutaneous ultrasound-guided radiofrequency electrocautery for the treatment of small hepatocellular carcinoma. J Intervent Radiol 1993; 8: 97–103; McGahan J P, Griffey S M, Budenz R W, Brock J M. Percutaneous ultrasound-guided radiofrequency electrocautery ablation of prostate tissue in dogs. Acad Radiol 1995; 2: 61–65; Goldwasser B, Ramon J, Engelberg S. Transurethral needle ablation (TUNA) of the prostate using low level radiofrequency energy: An animal experimental study. Eur Urol 1993; 24: 400–405; Goldberg S N, Gazelle G S, Dawson S L, Rittman W J, Mueller P R, Rosenthall D I. Tissue ablation with radiofrequency: Effect of probe size, gauge, duration, and temperature on lesion volume. Acad Radiol 1995; 2: 399–404). The longitudinal dimension, however, is simply dependent on the length of the uninsulated part of the electrode (see Goldberg S N, Gazelle G S, Dawson S L, Rittman W J, Mueller P R, Rosenthall D I. Tissue ablation with radiofrequency: Effect of probe size, gauge, duration, and temperature on lesion volume. Acad Radiol 1995; 2: 399–404).

Different strategies to increase lesion size by avoidance of charring have been studied: Pulsed RF energy delivery (see Nath S, Whayne J G, Haines D E. Does pulsed radiofrequency delivery result in greater tissue heating and lesion size from catheter ablation. PACE 1993; 16: 947); monitoring and controlling the power (see Wittkamp FHM, Hauer RNW, de Medina EOR. Control of radiofrequency lesion size by power regulation. Circulation 1989; 80: 962–968), impedance (see Strickberger S A, Hummel J D, Vorperian V R, et al. A randomized comparison of impedance and temperature monitoring during accesory pathway ablation. Circulation 1993; 88:I-295 (abstr)), and temperature (see Langberg J J, Calkins H, El-Atassi R, et al. Temperature monitoring during radiofrequency catheter ablatiom of accessory pathways. Circulation 1992; 86: 1469–1474; Sanchez R, vanSonnenberg E, Agostino H D, Goodacre B, Esch O. Percutaneous tissue ablation by radiofrequency thermal energy as a prelim to tumour ablation. Minimally Invasive Therapy 1993; 2: 299–305); needle electrodes with either a large radius (see Haines D E, Watson D D, Verow A F. Electrode radius predicts lesion during radiofrequency energy heating. Validation of a proposed thermodynamic model. Circ Res 1990; 67: 124–129), or made by precious metals (see Sanchez R, vanSonnenberg E, Agostino H D, Goodacre B, Esch O. Percutaneous tissue ablation by radiofrequency thermal energy as a prelim to tumour ablation. Minimally Invasive Therapy 1993; 2: 299–305); multi needle electrode application (see Goldberg S N, Gazelle G S, Dawson S L, Rittman W J, Mueller P R, Rosenthall D I. Tissue ablation with radiofrequency using multiprobe arrays. Acad Radiol 1995; 2: 670–674); porous RF needle electrodes for saline tissue irrigation (see Goldberg S N, Gazelle G S, Solbiati L, Monti F, Livraghi T, Rittman W J. Saline-enhanced RF tissue ablation: Demonstration of efficacy and optimization of parameters. Radiology 1995; 197 (P): 140 (abstr)); and expansible electrodes (see Reidenbach HD. First experimental results with special applicators for high-frequency interstitial thermotherapy. Minimally Invasive Therapy 1995; 4 (Suppl 1): 40 (abstr)). The background prior art has furthermore been disclosed in International Applications WO 95/05212; WO 94/10924; WO 94/11059; U.S. Pat. Nos. 5,342,357; 5,348,554; 5,334,193; 5,122,137; 5,383,876; 4,532,924; EP Patent Application Nos. 246,350; 480,639; 274,118; 105,677; 368,161, 608,609; Danish Patent No. 169,644; and DE Offenlegungsschrift 2,407,559. Reference is made to the above patents and patent applications, of which the U.S. patents are hereby incorporated by reference.

SUMMARY OF THE INVENTION

An object of the present invention is to provide an electrosurgical instrument which avoids the disadvantages of the prior art electrosurgical instruments.

Another object of the present invention is to prevent charring around the distal end of an electrosurgical instrument.

A further object of the present invention is to provide a lesion of any specific size.

A still further object of the present invention is to provide an apparatus for tissue ablation.

A further object of the present invention is to provide a method for treating damaged or diseased tissue from a mammal.

An even further object of the present invention is to provide larger lesions than hitherto reported.

In a first aspect, the present invention provides an electrosurgical instrument for tissue ablation, comprising:

i) an elongated tubular element defining a distal end and a proximal end, the distal end being configured so as to allow the distal end to perforate and penetrate into tissue, and the distal end being exposed for establishing electric and thermal communication to the tissue, ii) a cooling fluid passage housed within the elongated tubular element and establishing fluid communication from a cooling fluid input provided at the proximal end of the elongated tubular element to the distal end for establishing heat conductive communication therewith and from the distal end to a cooling fluid output provided at the proximal end of the elongated tubular element, and iii) an electric conductor means provided at the proximal end of the elongated tubular element and establishing electric conductive communication with the distal end for the supply of electric energy to the distal end so as to establish the tissue ablation through the supply of electric energy to the tissue from the distal end and so as to prevent charring of the tissue through cooling the distal end of the tubular elongated element by the supply of cooling fluid to the distal end through the cooling fluid passage.

In the present context, the expression "communication" is to be construed a generic term comprising the technique of establishing communication for the transfer of electric energy between any two components or elements, and the expression is to be construed comprising conventional expressions such as contact, connection, etc., conventionally used in the context of transferring electric energy and/or heat.

In the present context, the term "AC" means alternating current, the term "DC" means direct current, and the term "RF" means radiofrequency, i.e. alternating currents of a frequency useful for radiotransmission such as a frequency between 10 kHz and 100,000 MHz or even higher.

In a first embodiment of the electrosurgical instrument according to the first aspect of to the invention, the cooling fluid passage comprises an inner tube extending co-axially with and essentially in the entire length of the elongated tubular element, wherein the inner tube has an open end portion at the distal end communicating with the distal end of the elongated tubular element, and an opposite open end portion at the proximal end communicating with the cooling fluid output.

In a second embodiment of the electrosurgical instrument according to the first aspect of the invention, the cooling fluid passage comprises an inner tube extending co-axially with and essentially in the entire length of the elongated tubular element, wherein the inner tube has an open end portion at the distal end communicating with the distal end of the elongated tubular element, and an opposite open end portion at the proximal end communicating with the cooling fluid input.

In a first alternative embodiment of the electrosurgical instrument according to the first aspect of the invention, the inner tube has an end portion at the distal end provided with a number of holes for supplying the cooling fluid to the distal end of the elongated tubular element.

In a second alternative embodiment of the electrosurgical instrument according to the first aspect of the invention, the inner tube has a helical structure at the distal end of the elongated tubular element.

In a third alternative embodiment of the electrosurgical instrument according to the first aspect of the invention, the inner tube is made of a flexible material.

In a third embodiment of the electrosurgical instrument according to the first aspect of the invention, the tubular elongated element comprises an inner partition wall extending essentially in the entire length of the elongated tubular element and defining an input and an output part of the cooling fluid passage.

In a fourth alternative embodiment of the electrosurgical instrument according to the first aspect of the invention, the elongated tubular element is provided with an insulating material, the insulating material surrounding the elongated tubular element and extending along the elongated tubular element from the proximal end to the distal end so as to provide an exposed distal end.

In a fifth alternative embodiment of the electrosurgical instrument according to the first aspect of the invention, the insulating material levels with the exposed distal end of the elongated tubular element.

It might appear strange to establish a cooling mechanism to an electrosurgical instrument inserted interstitially for tissue ablation by heating. The cooling mechanism, however, causes a marked increase in lesion size by prolonging the duration of DC or AC, preferably RF delivery when compared to the situation without cooling. About 20% of the applied RF power and energy is absorbed by cooling in the range of 40–50 W (cf. Table 2). This part of delivered effect and energy is transformed to heating of the cooling fluid, e.g. water, in the reservoir.

The observed significant increase in lesion size obtained with the electrosurgical instrument was seen in the range of 20 to 50 W in generator output power. In this interval a significant increase in duration of RF delivery was observed as a result of prevention or delay of charring. This leads to a significant increase in delivered energy followed by increased lesion size. Charring was, however, seen when the power exceeded 50 W. A more effective cooling of the needle may prevent this with subsequent larger lesions. This could be achieved by an increased irrigation flow or by the use of chilled water or other cooling agents.

In a further embodiment of the electrosurgical instrument, the exposed distal end of the electrosurgical instrument has a length in the range of 1 mm to 1000 mm, e.g. 1 mm to 5 mm, 1 mm to 10 mm, 1 mm to 20 mm, 1 mm to 30 mm, 1 mm to 40 mm, 1 mm to 50 mm, 1 mm to 100 mm, 1 mm to 200 mm, 1 mm to 300 mm, 1 mm to 400 mm, 1 mm to 500 mm, 1 mm to 600 mm, 1 mm to 700 mm, 1 mm to 800 mm, 1 mm to 900 mm, 1 mm to 1000 mm, such as 1 mm to 5 mm, 5 mm to 10 mm, 10 mm to 20 mm, 20 mm to 30 mm, 30 mm to 40 mm, 40 mm to 50 mm, 50 mm to 100 mm, 100 mm to 200 mm, 200 mm to 300 mm, 300 mm to 400 mm, 400 mm to 500 mm, 500 mm to 600 mm, 600 mm to 700 mm, 700 mm to 800 mm, 800 mm to 900 mm, and 900 mm to 1000 mm.

The shape of a DC or AC, preferably RF lesion is a prolate ellipsoid centered around the uninsulated portion of the electrode tip. In the present study, however, high energy delivery mainly affected the coagulation depth (transverse diameter) resulting in almost spherical lesions. A 2 cm uninsulated needle tip gave lesions with a diameter of about 4 cm. A 3 cm uninsulated may result in lesions with a diameter of about 6 cm if the output power and the cooling mechanism are adjusted to this dimension. Formation of spherical lesions is an advantage in clinical use, since the neoplastic lesions being treated often are spheric.

In a still further embodiment of the electrosurgical instrument, the distal end of the electrosurgical instrument has a transverse diameter i the range of 0.1 mm to 5 mm, e.g. 0.1 mm to 0.4 mm, 0.1 mm to 0.6 mm, 0.1 mm to 0.8 mm, 0.1 mm to 1.0 mm, 0.1 mm to 1.2 mm, 0.1 mm to 1.4 mm, 0.1 mm to 1.6 mm, 0.1 mm to 1.8 mm, 0.1 mm to 2.0 mm, 0.1 mm to 3.0 mm, 0.1 to 4.0 mm, 0.1 mm to 5.0 mm, such as 0.1 mm to 0.4 mm, 0.4 mm to 0.6 mm, 0.6 mm to 0.8 mm, 0.8 mm to 1.0 mm, 1.0 mm to 1.2 mm, 1.2 mm to 1.4 mm, 1.4 mm to 1.6 mm, 1.6 mm to 1.8 mm, 1.8 mm to 2.0 mm, 2.0 mm to 3.0 mm, 3.0 mm to 4.0 mm, and 4.0 mm to 5.0 mm.

A 2 mm (14 gauge) needle electrode is probably the largest dimension in percutaneous RF treatment. A larger needle electrode would be associated with a increased risk of hemorrhage from the puncture track. A smaller needle diameter, i.e. 1.2 mm (18 gauge), would be easier to insert into a tumor guided by imaging. This needle dimension might give the same lesions as the 2.0 mm needle in the present study, if the output power and cooling mechanism are adjusted. A larger needle i.e. 3 mm, might have the potential to produce very large lesions and could be useful during surgery in treatment of liver tumors, similar to cryosurgery.

In the present study only macroscopic evaluation of tissue coagulation is performed. In vivo evaluation of a RF lesion should include microscopy and electronmicroscopy since a rim with inflammatory changes of non-coagulated but non-vital liver tissue will surround the macroscopically coagulated area. The size of destructed tissue in vivo will therefore be larger than seen in vitro. On the other hand will in vivo performance be affected by heat loss because of blood circulation (conduction), which will tend towards a smaller lesion.

In a further embodiment of the electrosurgical instrument, the cooling fluid is selected from liquid material and gaseous material and mixtures thereof, the fluid serving to limit the heat transfer from the needle electrode to adjacent tissue to an extent sufficient to prevent charring around the distal end of the elongated tubular element.

In a still further embodiment of the electrosurgical instrument, the cooling fluid is biologically acceptable and/or compatible with tissue from a mammal and is selected from water, saline, air, nitrogen or the like and mixtures thereof.

In a second aspect, the present invention provides an apparatus for tissue ablation, comprising:

an electrosurgical instrument for tissue ablation, the instrument comprising:

i) an elongated tubular element defining a distal end and a proximal end, the distal end being configured so as to allow the distal end to perforate and penetrate into tissue, and the distal end being exposed for establishing electric and thermal communication to the tissue, ii) a cooling fluid passage housed within the elongated tubular element and establishing fluid communication from a cooling fluid input provided at the proximal end of the elongated tubular element to the distal end for establishing heat conductive communication therewith and from the distal end to a cooling fluid output provided at the proximal end of the elongated tubular element, and iii) an electric conductor means provided at the proximal end of the elongated tubular element and establishing electric conductive communication with the distal end for the supply of electric energy to the distal end so as to establish the tissue ablation through the supply of electric energy to the tissue from the distal end and so as to prevent charring of the tissue through cooling the distal end of the tubular elongated element by the supply of cooling fluid to the distal end through the cooling fluid passage, means for supplying the cooling fluid to the cooling fluid input of the elongated tubular element, a neutral electrode means, and an electric energy source for establishing an electric circuit through the electrosurgical instrument, the tissue and the neutral electrode means and for supplying the electric energy to the distal end.

In a first embodiment of the apparatus according to the second aspect of the present invention, the electrosurgical instrument has any of the features of the electrosurgical instrument according to the first aspect of the invention.

In a further embodiment of the apparatus according to the second aspect of the invention, the netural electrode means is constituted by a further electrosurgical instrument according to any of the above embodiments of the electrosurgical instrument according to the first aspect of the invention, and the apparatus constitutes a bipolar electrosurgical apparatus.

In a third aspect, the present invention provides a method for providing a lesion in damaged or diseased tissue from a mammal, comprising:

providing an electrosurgical instrument for tissue ablation, the instrument comprising:

i) an elongated tubular element defining a distal end and a proximal end, the distal end being configured so as to allow the distal end to perforate and penetrate into tissue, and the distal end being exposed for establishing electric and thermal communication to the tissue, ii) a cooling fluid passage housed within the elongated tubular element and establishing fluid communication from a cooling fluid input provided at the promixal end of the elongated tubular element to the distal end for establishing heat conductive communication therewith and from the distal end to a cooling fluid output provided at the proximal end of the elongated tubular element, and iii) an electric conductor means provided at the proximal end of the elongated tubular element and establishing electric conductive communication with the distal end for the supply of electric energy to the distal end, perforating the tissue by means of the elongated tubular element and penetrating the elongated tubular element into the tissue, providing a means for supplying the cooling fluid and connecting the cooling fluid supplying means to the input provided at the proximal end of the elongated tubular element of the electrosurgical instrument, providing a neutral electrode means and connecting the counter electrode means to the mammal for establishing electric communication therewith, providing an electric energy source for generating the electric energy and connecting the electric energy source to the electric conductor means of the electrosurgical instrument and to the neutral electrode means, and supplying electric energy from the electric energy source to the distal end of the elongated tubular element of the electrosurgical instrument for establishing the tissue ablation and at the same time supplying the cooling fluid to the distal end of the elongated tubular element of the electrosurgical instrument for preventing charring of the tissue for cooling the distal end, thereby providing a lesion of a specific volume within the tissue.

In a first embodiment of the method according to the third aspect of the invention, the electrosurgical instrument has any of the features of the electrosurgical instrument according to any of the above embodiments of the electrosurgical instrument, and/or the electrosurgical instrument constitutes the electrosurgical instrument of the apparatus according to any of the embodiments of the apparatus.

In a second embodiment of the method according to the third aspect of the invention, the damaged or diseased tissue comprises a tumor.

In third embodiment of the method according to the third aspect of the present invention, the electric energy source constitutes a timer controlled constant power RF generator generating a power output of 10–20 W, 20–30 W, 30–40 W, 40–50 W, 50–60 W, 60–70 W of a frequency of 10–20 kHz, 20–40 kHz, 40–80 kHz, 80–160 kHz, 160–320 kHz, 320–640 kHz, 640–1280 kHz, 1280–2560, 2560–5120 kHz, 5120 kHz-10 MHz, 10–20 MHz, 20–40 MHz, 40–80 MHz, 80–160 MHz, 160–320 MHz, 320–640 MHz, 640–1280 MHz, 1280–2560 MHz, 2560–5120 MHz, 5120–10,000 MHz, 10,000–20,000 MHz, 20,000–40,000 MHz, 40,000–80,000 MHz, 80,000–100,000 MHz.

A comparison study of the electrosurgical instrument of the invention with a conventional needle electrode is performed. A maximum ablation period of 10 minutes was chosen in the present study for making the comparison between the two needle electrodes easier. If no maximum ablation duration had been chosen, more energy could have been delivered using the cooled needle electrode in the range of 20 to 40 W, and even bigger lesions might have been the result. In clinical use a short treatment duration is desirable because of lower rate of anaesthetic complications.

The thermo camera study showed an interesting difference in temperature distribution between the two needle electrode types. When the cooled needle electrode was used, the hottest part of the lesion was not adjacent to the needle electrode, but in a concentric ring a few mm from the exposed (non-insulated) part of the needle. It was noteworthy to see, that the tissue temperature in this ring was about 100° C. even at 40 W after 5 minutes while the needle temperature was about 50–60° C. No charring was observed within 10 minutes application of 40 W. This part of the study illustrates, that measurement of the needle electrode tip temperature does not give direct information about the temperature in the critical zone in the lesion where charring is expected, namely a concentric ring 2–3 mm from the needle electrode tip. Measurement of this temperature may theoretically be obtained by using thermocouples inserted into the zone. Changes in needle tip temperature may, however, predict occurrence of charring, which also may be predicted by the change in afferent cooling water temperature.

The temperature distribution explains the lack of needle electrode adhesion even after occurrence of charring with the cooled needle electrode: The part of tissue within the concentric ring of charring is coagulated and not carbonized because of the cooling effect. This is relevant in clinical use because adhesion during needle electrode removal may cause tissue damage and hemorrhage.

Larger spherical lesions can now be produced with the electrosurgical instrument of the invention which furthermore is a low cost technology when compared to laser, cryo, and microwave.

BRIEF DESCRIPTION OF THE DRAWINGS

The invention will now be described with reference to the drawings, wherein

FIG. 1 is a cross-sectional view of a cooled needle electrode according to a first and preferred embodiment of the invention for radiofrequency tissue ablation;

FIG. 2a is a broken-away partly perspective cross-sectional view of the tip part of the cooled needle electrode according to the first embodiment of the invention shown in FIG. 1;

FIG. 2b is a broken-away cross-sectional view of a second embodiment of the cooled needle electrode shown in FIG. 2a;

FIG. 2c is a broken-away cross-sectional view of a third embodiment of the cooled needle electrode shown in FIG. 2a;

FIG. 2d is a broken-away cross-sectional view of a fourth embodiment of the cooled needle electrode shown in FIG. 2a;

FIG. 2e is a broken-away cross-sectional view of a fifth embodiment of the cooled needle electrode shown in FIG. 2a;

FIG. 2f is a broken-away partly cross-sectional view of a sixth embodiment of the cooled needle electrode shown in FIG. 2a to 2e;

FIG. 3 is an overall schematic view of an apparatus according to a first and preferred embodiment of the invention showing the use of the cooled needle electrode of FIG. 1 for providing a lesion in a calf's liver;

FIG. 4 is a broken-away perspective view of the cooled needle electrode according to FIG. 2a to 2d;

FIG. 5a is a schematic perspective view of the temperature distribution in a RF lesion produced with a cooled needle electrode according to a first and preferred embodiment of the invention;

FIG. 5b is a schematic perspective view of the temperature distribution in a RF lesion produced with a conventional needle electrode;

FIG. 6 is a graphical view of the behaviour of the current with increasing temperature of the area surrounding the cooled needle electrode according to a first and preferred embodiment of the invention.

DETAILED DESCRIPTION OF THE PREFERRED EMBODIMENTS

Figure 7:
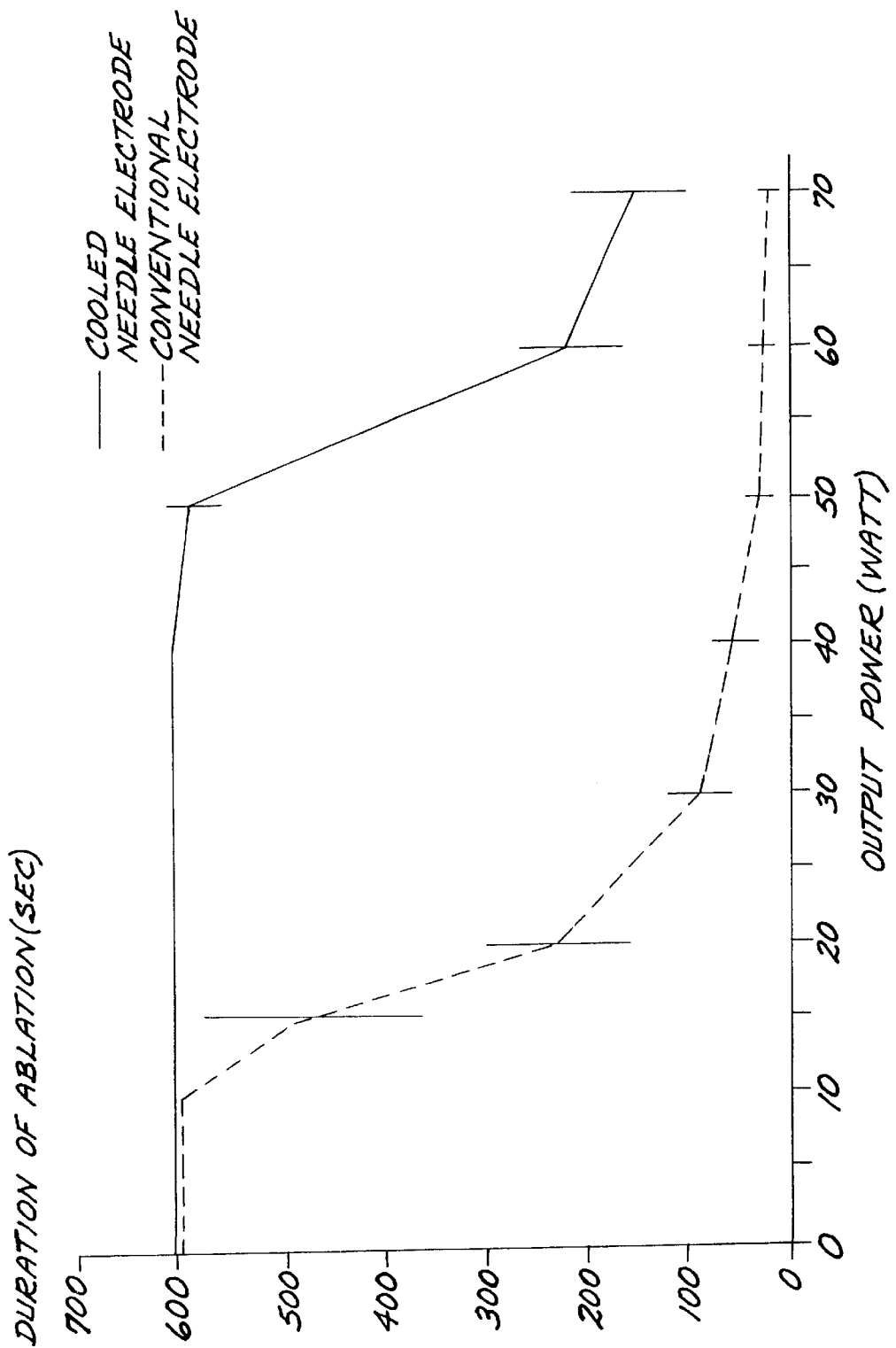
FIG. 7 is a graphical view of RF lesions produced with a cooled needle electrode of the invention and a conventionel needle electrode, showing the influence of output effect on duration of ablation.

In FIG. 1 a first and preferred embodiment of the cooled needle electrode 10 according to the invention is shown. The needle electrode 10 is made of stainless steel, however, any material suitable for insertion into tissue may be used. The cooled needle electrode 10 has a distal 16 and a proximal 20 end and comprises an outer tube 14 having a tip part 16 which is exposed and a tip point 16' which is construed so as to penetrate tissue with a minimum risk of hemorrhage from the puncture tract. The non-exposed part of the outer tube 14 is surrounded by an insulating material 12. The insulating material 12 may be any material which is biologically acceptable and suitable for insertion into tissue. The distal 2 cm of the electrode 10 is non-insulated and thereby exposed for DC or AC, preferably RF delivery. An inner tube 18 is provided inside the tube 14 co-axially with the outer tube 14. The outer tube 14 has a transverse diameter of 2 mm (14-gauge). An adapter 20 is provided at the proximal end 20 opposite the tip part 16. The adapter 20 is equipped with a line 22, the line 22 being connected to the inner tube 18 and communicating therewith for providing a cooling fluidum such as water to the exposed part at the distal end 16. The water is led through the inner tube 18 to the tip part 16 and away from the tip part through the interior of the outer tube 14. The outer tube 14 is connected to and communicates with a line 24 for discharge of the cooling water. The lines 22 and 24 communicates with a cooling water reservoir (not shown). Circulation of the cooling water is established with a pump (not shown). The outer tube 14 of the cooled needle electrode 10 is connected to a RF electrosurgical generator (not shown) through line 26 for providing power to the cooled needle electrode 10.

In FIG. 2a the tip part 16 of the cooled needle electrode 10 of FIG. 1 is shown. The cooling water flows through the inner tube 18 and out at a tip 28 of the inner tube 18 and flows into the tip part 16 and out of the outer tube 14 shown at 30 for thereby providing a cooled needle electrode 10.

In FIG. 2b a second embodiment of the tip part 16 of the cooled needle electrode 10 of FIG. 2a is shown. The cooling water flows through an inner tube 32 and out of holes 34 and flows into the tip part 16 and out of the outer tube 14 for thereby providing a cooled needle electode 10.

In FIG. 2c a third embodiment of the tip part 16 of the cooled needle electrode 10 of FIG. 2a is shown. The cooling water flows through an inner tube 36 having a helical structure 38 at the exposed part of the tip part 16 of the cooled needle electrode 10 and flows into the tip part 16 and out of the outer tube 14 thereby providing a cooled needle electrode 10.

In FIG. 2d a fourth embodiment of the tip part 16 of the cooled needle electrode 10 of FIG. 2a is shown. The cooling water flows through a flexible inner tube 40 and out of holes 42 and flows into the tip part 16 and out of the outer tube 14 for thereby providing a cooled needle electrode 10.

In FIG. 2e a fifth embodiment of the tip part 16 of the cooled needle electrode 10 of FIG. 2a is shown. The internal portion of the outer tube 14 is separated by a wall 44 for thereby leading the cooling water shown at 46 into the tip part 16 of the cooled needle electrode 10 and away from the tip part shown at 48 for thereby providing a cooled needle electrode 10.

In FIG. 2f a sixth embodiment of the tip part 16 of the cooled needle electrode 10 of FIG. 2a to 2d is shown. The insulation 12' is provided on the surface of the outer tube 52 and levels with the exposed part of the outer tube 50 shown at 54 for thereby providing a cooled needle electrode 10 which is easier to insert into tissue.

In FIG. 3 a first and preferred embodiment of the apparatus according to the invention is shown. The apparatus comprises a RF electrosurgical generator 60 and a line 62 connected to and communicating with a neutral plate 64 and the line 26 for power supply to the electrode 10. The electrode 10 protrudes into a calf's liver 66 placed on the neutral plate 64 and thereby creates a lesion 68. Cooling water 74 is supplied from a reservoir 72 to the electrode 10 through the line 22 and the water is led back to the water reservoir 72 through the line 24 by means of pump 70 which provides circulation of the cooling water 74. A thermosensor 80 is connected to the lines 22 and 24 through lines 76 and 78, respectively, for measuring the temperature of the cooling water flowing into the cooled needle electrode 10 through line 22 and away from the cooled needle electrode 10 through line 24.

In FIG. 4 the cooled needle electrode 10 of FIG. 2a to 2d is shown. During the use of the electrode 10 the cooling of the tip part 16 by way of supplying cooling water as discussed above provides water droplets shown at 82 on the exposed surface of the outer tube 14 and the tip part 16 of the cooled needle electrode 10.

In FIG. 5a the temperature distribution in a RF lesion in calf's liver produced with a cooled needle electrode of the invention is shown. A temperature fall around the needle electrode is observed and charring around the cooled needle electrode is not produced, if not eliminated.

In FIG. 5b the temperature distribution in a RF lesion in calf's liver produced with a conventional electrode is shown. No temperature fall around the electrode is observed; in fact a very steep temperature gradient is observed and charring around the conventional electrode occurs shortly after commenced treatment.

In FIG. 6 the graphical view of the behaviour of the current with increasing temperature of the area surrounding the cooled needle electrode of the invention is shown. As the lesion current drops and no further energy is delivered around the electrode of the invention due to charring around the electrode, no further tissue heating occurs.

Figure 8:
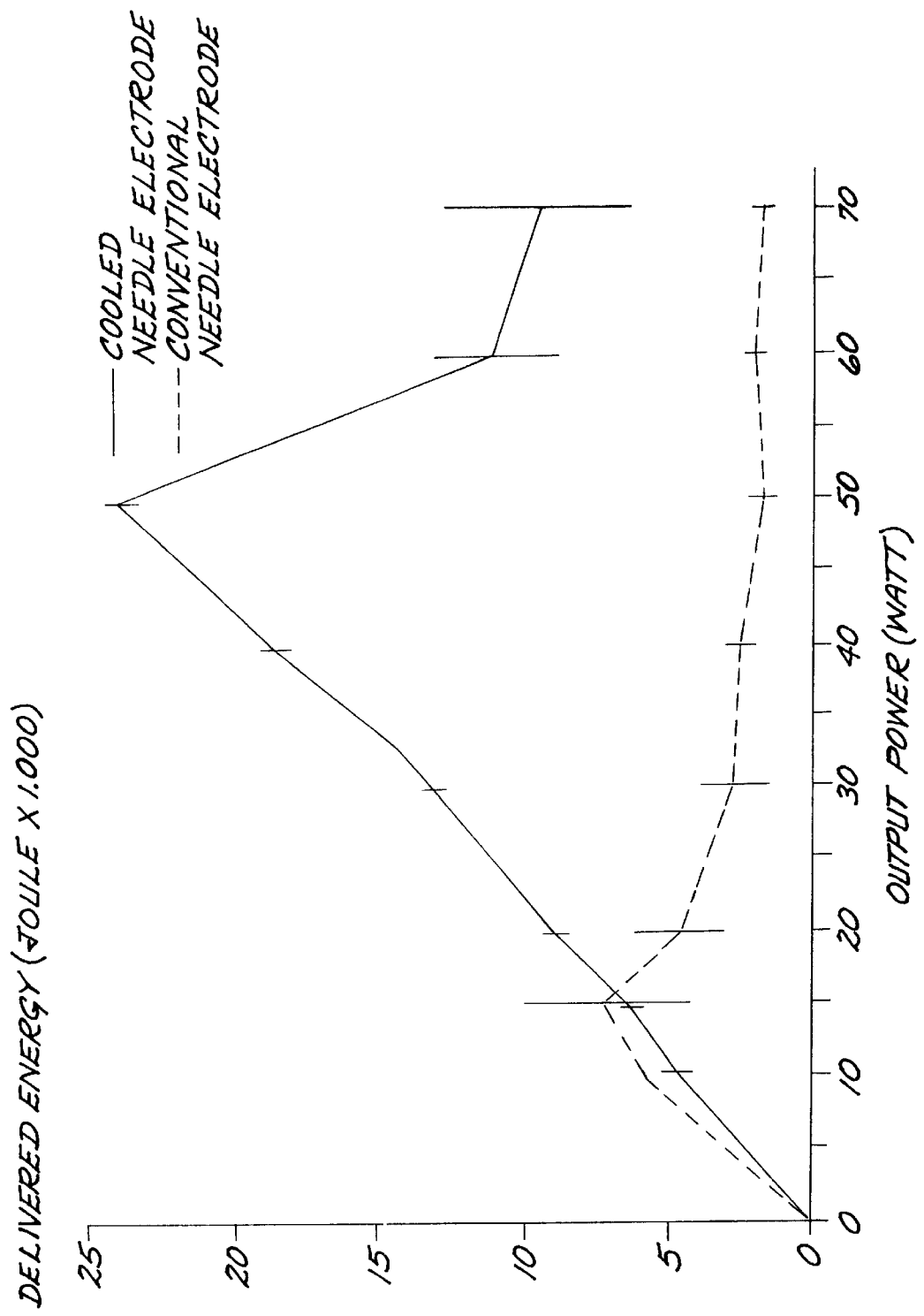
FIG. 8 is a graphical view of RF lesions produced with a cooled needle electrode of the invention and a conventionel needle electrode, showing the influence of output effect on delivered energy.
Figure 9:
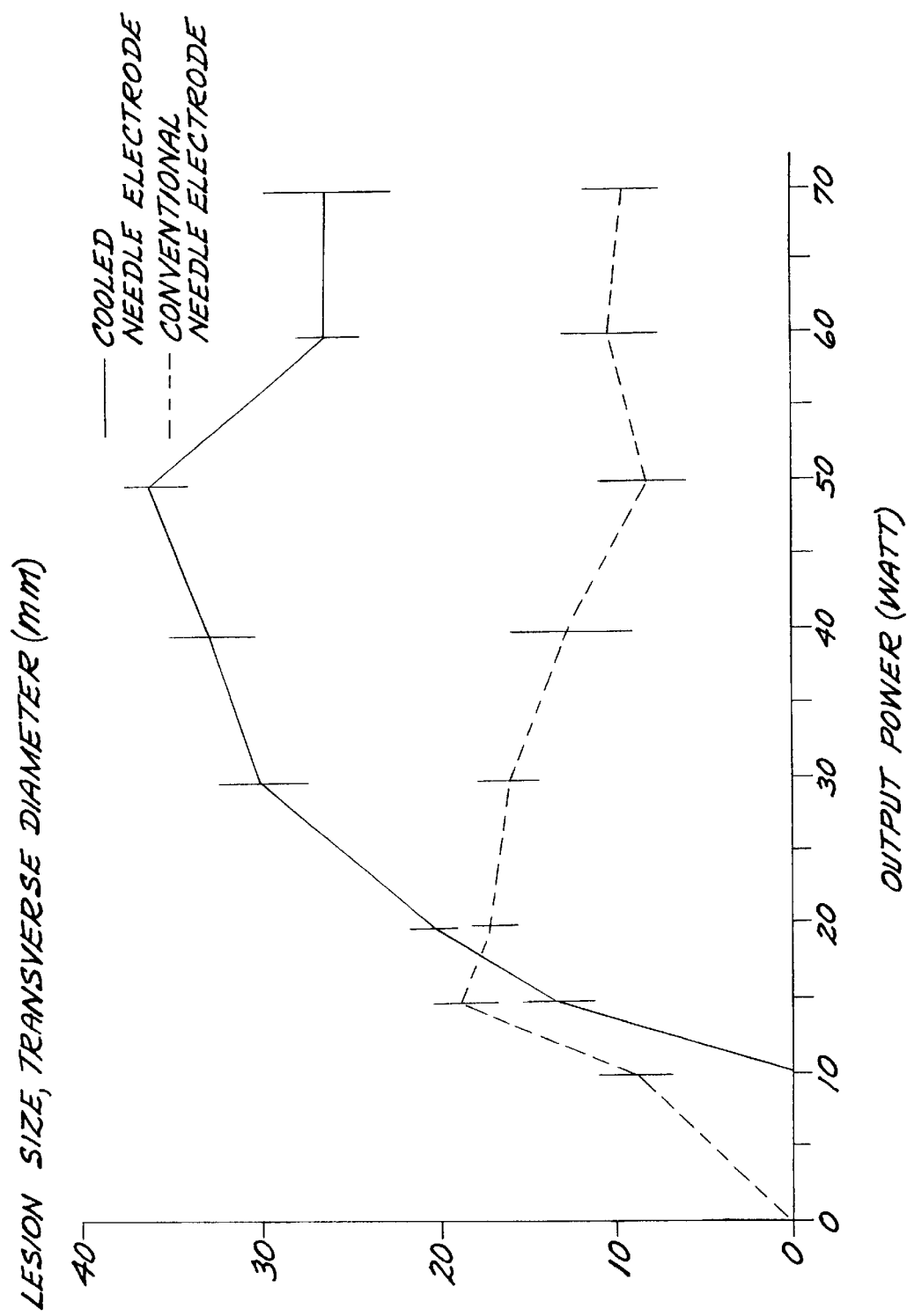
FIG. 9 is a graphical view of RF lesions produced with a cooled needle electrode of the invention and a conventional needle electrode, showing the influence of output effect on lesion size.

In FIGS. 7 to 9 graphical views of RF lesions produced with a cooled needle electrode and a conventional needle electrode are shown. The influence of output effect on duration of ablation, delivered energy and lesion size, respectively, obtained with the two needle electrode types is shown.

The invention will now be further illustrated in the experimental part, which by no means should be construed as limiting the scope of the present invention.

EXPERIMENTAL PART:

A specially designed 2 mm (14-gauge) cooling needle electrode was used. The distal 2 cm of the needle electrode was uninsulated (FIG. 1). For water circulation, an inner tube was placed inside the outer needle (FIG. 2a). Via tubings the two needle lumina were connected to a reservoir containing approximately 1 liter of cooling water (tap water with room temperature). Circulation of cooling water was established with a pump, flow rate 56 mL/min. The water flowed towards the needle tip via the inner tube and returned via the lumen between the outer needle and inner tube (FIG. 3). Thus, no circulating water came in a direct contact with the tissue. The cooling effect was a result of irrigation of the needle tip from the inside. The conventional needle electrode had the same dimensions as the outer needle above.

The needle electrodes were connected to a RF electrosurgical generator (Erbotom ICC 300, Erbe USA INC, Atlanta). In the cut mode, this generator produces an unmodulated sinusoid waveform of RF voltage with a frequency of 350 KHz. The output power can be changed from 0 to 300 Watts (W) with a voltage output up to 350 Volts dependent on the tissue impedance. The operator can limit the maximum voltage output in four steps (level 1 to 4) from 150 to 350 Volts. Level 4 in the cut mode was chosen in the present study. The current to the generator was monitored with an amperemeter interpositioned between the generator and the power supply (FIG. 3).

The first series was undertaken for a quantitative evaluation of the RF energy delivered around the needle electrode and the size of the correspondent lesion when different levels of generator output power were applied to the two needle electrode types in fixed periods of 10 minutes. Three procedures were performed with each power level. Fresh calf's liver was placed on a neutral plate connected to the generator. The amount of thermal energy carried away from the electrode due to the cooling effect was monitored by measuring the afferent and efferent water temperatures with fluoroptic thermal fiber probes (Model 3000, Luxtron, Calif., USA). The fibers were placed inside the tubings in direct contact to the circulating water (FIG. 3). The temperature measurement system did not interfere with the RF current.

The duration of ablation=the time until occurrence of charring was measured with a stopwatch. The procedure was terminated (RF generator and circulation pump turned off), after 10 minutes if no charring had occurred. Criteria for occurrence of charring included an audible pop from the heated tissue associated with generator current falling to the basis level. On subsequent macroscopic examination of the liver, the size of the coagulated area was measured with a ruler or a slide gauge. Longitudinal dimension was parallel to the needle axis, transverse diameter was perpendicular to the needle axis. No microscopy was done.

Calculation of delivered energy (Joule) around the needle electrode tip was done as follows: With the conventional needle electrode the delivered energy is equal to the RF energy, namely the product of the output effect (Watt) and the duration of ablation (sec). With the cooled needle electrode the delivered energy is the RF energy minus the energy absorbed by cooling water. The latter parameter was calculated using the formula $Q=m \cdot c \cdot t$, where m is the mass of water (flow rate [56 ml/sec]×density [1 g/ml]×duration of ablation [sec]), c is the heat capacity of water (4.19 Joule/g °C.), and t is the average difference between the temperature in the efferent and afferent cooling water (°C.). Heat loss in the needles was not taken into account.

For statistical analysis, the data from this part of the study were evaluated with a t-test, level of significance being 0.05.

The second series was undertaken for a qualitative evaluation of the temperature distribution in tissue around the cooling needle electrode compared to a conventional needle electrode. Fresh calf's liver was placed in a metal cylinder (diameter 8 cm, height 5 cm) connected to the neutral socket of the generator. The cylinder containing calf's liver was positioned near vertically. The needle electrode was inserted centrally into the liver (posterior surface) and advanced until the tip was just visible and palpable on the opposite surface. This surface was examined with an infrared thermo imaging system (AGA, Germany). With a generator setting of 40 W, thermo images were recorded with 30 sec intervals in a 5 min period with both types of electrodes. Images were stored on a floppy disc for further postprocessing.

In both series, the temperature of the liver and cooling water was room temperature.

Results from the first series using a conventional needle electrode and a cooled needle electrode are listed in Tables 1 and 2, respectively. The difference between the temperature in the afferent and efferent cooling water showed a slight increase during the 10 minutes of ablation or until occurrence of charring. This is illustrated with the changes in temperature difference in one of the three procedures obtained at 40 W: The temperature difference was 1.8; 2.3; 2.5; 2.6; and 2.6° C. after 2; 4; 6; 8; and 10 minutes, thus giving one observation with an average temperature difference of 2.4° C. FIGS. 7 to 9 show duration of ablation, delivered energy, and lesion size (transverse diameter) obtained with the two needle electrode types.

At 10 W, no charring was observed with the two needle electrodes in the period of 10 minutes of RF application. Because of absorbed cooled energy, the delivered energy and lesion size were smaller when the cooling needle was used.

At 15 W the conventional needle had its optimum concerning delivered energy and lesion size (mean 19 mm).

In the range of 20 to 70 W, however, the cooled needle was significantly superior to the conventional needle concerning the duration of ablation, delivered energy, and lesion size. With the cooled needle electrode charring was first observed at 50 W. At this level, the cooled needle electrode had its optimum concerning delivered energy and lesion size (mean 36 mm).

On macroscopic evaluation the lesions were homogeneous, whitish because of coagulation. The border between coagulated and non-coagulated liver tissue was well-defined, specially when the output effect exceeded 20 W. The longitudinal shape of the lesions was dependent on the amount of delivered energy. In the low range of delivered energy an ellipsoid lesion was produced. The lesions became increasingly spherical with higher amounts of delivered energy. The largest lesion was obtained with the cooled needle electrode at 50 W and measured 37 mm in transverse diameter and 41 mm in longitudinal dimension. When charring was observed using the cooled needle electrode, the macroscopic evaluation showed a concentric ring (thickness 1 mm) of char approximately 3 mm from the needle track. In transverse section of RF lesions made with a cooled needle electrode, no charring was observed in a lesion produced with 40 W in 10 minutes. In transverse section of RF lesions made with a cooled needle electrode charring occurred after 9 minutes in a lesion produced with 50 W. A concentric ring around the needle track centrally represents charring. Transverse diameter of coagulation was 35 cm. Coagulated liver tissue was seen between the needle tract and the charred ring. In comparison, if charring had terminated the procedure using the conventional needle, macroscopy showed char adjacent to the needle track. In these cases it was difficult to remove the needle electrode from the lesion because of agglutination of liver tissue to the uninsulated part of the needle. This phenomenon was not observed when the cooled needle electrode was removed from a lesion. Even after occurrence of charring, this needle electrode appeared without char and tissue adhesions.

The temperature distribution in calf's liver tissue around the cooled needle electrode and the conventional needle electrode is shown in FIG. 5a and FIG. 5b, respectively. Charring around the conventional needle electrode occurred after approximately 30 seconds where the temperature at the needle tip was about 200° C. and a very steep temperature gradient was observed (FIG. 5b). No charring around the cooled needle electrode was observed within the 5 minutes of RF heating at 40 watt. At the end of this procedure, the temperature at the point of the needle tip was in the range of 49.8 to 63.5° C. The maximum temperatures were seen in a concentric ring 2 to 3 mm from the needle and were in the range of 97.6 to 102° C. (FIG. 5a).

TABLE 1

RF Liver Ablation in 10 Minutes with a Conventional Needle Electrode

|  | Output effect (Watt) | | | | | | | |
| --- | --- | --- | --- | --- | --- | --- | --- | --- |
|  | 10 | 15 | 20 | 30 | 40 | 50 | 60 | 70 |
| Duration of ablation (sec) | 600* | 486 | 225 | 89 | 60 | 30 | 28 | 21 |
| Delivered Energy (Joule × 1,000) | 6.00 | 7.29 | 4.51 | 2.67 | 2.40 | 1.52 | 1.70 | 1.47 |
| Lesion size |  |  |  |  |  |  |  |  |
| transverse diameter (mm) | 9 | 19 | 17 | 16 | 12 | 8 | 10 | 9 |
| longitudinal dimension (mm) | 24 | 30 | 28 | 28 | 27 | 25 | 24 | 24 |

Note. - Values represent mean of three procedures.
*no charring was observed during 10 minutes of RF ablation.

TABLE 2

RF Liver Ablation in 10 Minutes with a Cooled Needle Electrode

|  | Output effect (Watt) | | | | | | | |
| --- | --- | --- | --- | --- | --- | --- | --- | --- |
|  | 10 | 15 | 20 | 30 | 40 | 50 | 60 | 70 |
| Duration of ablation (sec) | 600* | 600* | 600* | 600* | 600* | 592 | 215 | 155 |
| RF Energy (Joule × 1,000) | 6.00 | 9.00 | 12.0 | 18.0 | 24.0 | 29.6 | 12.9 | 10.8 |
| Temperature difference in cooling water (° C.) | 0.5 | 1.0 | 1.3 | 2.1 | 2.3 | 2.5 | 2.7 | 3.0 |
| Absorbed energy by cooling water (Joule × 1,000) | 1.25 | 2.43 | 3.05 | 4.93 | 5.47 | 5.71 | 2.14 | 1.82 |
| Delivered Energy (Joule × 1,000) | 4.75 | 6.57 | 8.95 | 13.1 | 18.5 | 23.9 | 10.8 | 9.04 |
| Lesion size |  |  |  |  |  |  |  |  |
| transverse diameter (mm) | 0 | 14 | 20 | 30 | 33 | 36 | 26 | 26 |
| longitudinal dimension (mm) | 0 | 26 | 32 | 38 | 39 | 40 | 32 | 34 |

Note. - Values represent mean of three procedures.
*no charring was observed during 10 minutes of RF ablation.

What is claimed is:
1. An electrosurgical instrument for tissue ablation, comprising:
 an elongated rigid tubular element defining a distal end and a proximal end, said distal end being configured so as to allow said distal end to perforate and penetrate into tissue, said distal end being electrically and thermally conductive for establishing electric and thermal communication with said tissue;

an electrical conductor connected to said tubular element so as to establish electrically conductive communication with said distal end of said tubular element, thereby to supply electrical energy to said distal end for the ablation of said tissue proximate said distal end; and a cooling fluid passage within said tubular element and establishing fluid communication from a cooling fluid input at said proximal end of said tubular element to said distal end for establishing heat conductive communication therewith, and from said distal end to a cooling fluid output at said proximal end, whereby the cooling fluid effects a cooling of the distal end that substantially prevents charring of said tissue during the ablation.

2. The electrosurgical instrument according to claim 1, wherein said cooling fluid passage comprises an inner tube extending co-axially with and essentially in the entire length of said elongated tubular element, wherein said inner tube has an open end portion at said distal end communicating with said distal end of said elongated tubular element, and an opposite open end portion at said proximal end communicating with said cooling fluid output.

3. The electrosurgical instrument according to claim 1, wherein said cooling fluid passage comprises an inner tube extending co-axially with and essentially in the entire length of said elongated tubular element, wherein said inner tube has an open end portion at said distal end communicating with said distal end of said elongated tubular element, and an opposite open end portion at said proximal end communicating with said cooling fluid input.

4. The electrosurgical instrument according to claim 3, wherein said inner tube has an end portion at said distal end provided with a number of holes for supplying said cooling fluid to said distal end of said elongated tubular element.

5. The electrosurgical instrument according to claim 3, wherein said inner tube has a helical structure at said distal end of said elongated tubular element.

6. The electrosurgical instrument according to claim 3, wherein said inner tube is made of a flexible material.

7. The electrosurgical instrument according to claim 1, wherein said tubular elongated element comprises an inner partition wall extending essentially in the entire length of said elongated tubular element and defining an input and an output part of said cooling fluid passage.

8. The electrosurgical instrument according to any of claims 1 to 2, wherein said elongated tubular element is provided with an insulating material, said insulating material surrounding said elongated tubular element and extending along said elongated tubular element from said proximal end to said distal end so as to provide an exposed distal end.

9. The electrosurgical instrument according to claim 8, wherein said insulating material levels with said exposed distal end of said elongated tubular element.

10. The electrosurgical instrument according to claim 8, wherein said exposed distal end of said electrosurgical instrument has a length in the range of 1 mm to 1000 mm.

11. The electrosurgical instrument according to claim 8, wherein said distal end of said electrosurgical instrument has a transversal diameter in the range of 0.1 mm to 5.0 mm.

12. Apparatus for tissue ablation, comprising:
an electrosurgical instrument for tissue ablation, comprising:
i) an elongated rigid tubular element defining a distal end and a proximal end, said distal end being configured so as to allow said distal end to perforate and penetrate into tissue, said distal end being electrically and thermally conductive for establishing electric and thermal communication with said tissue;
ii) an electrical conductor connected to said tubular element so as to establish electrically conductive communication with said distal end, thereby to supply electrical energy to said distal end for the ablation of said tissue proximate said distal end; and
iii) a cooling fluid passage within said tubular element and establishing fluid communication from a cooling fluid input at said proximal end of said tubular element to said distal end for establishing heat conductive communication therewith, and from said distal end to a cooling fluid output at said proximal end, whereby the cooling fluid effects a cooling of the distal end that substantially prevents charring of said tissue during the ablation;

means for supplying said cooling fluid to said cooling fluid input;

a neutral electrode; and an electrical energy source for establishing an electrical circuit through said electrosurgical instrument, said tissue, and said neutral plate, thereby supplying electrical energy to said tissue through said conductor and said distal end of said tubular element so as to effect tissue ablation.

13. A method for forming a lesion in tissue in a mammal, comprising the steps of:
(a) providing an electrosurgical instrument for tissue ablation, comprising:
i) an elongated rigid tubular element defining a distal end and a proximal end, said distal end being configured so as to allow said distal end to perforate and penetrate into tissue, said distal end being electrically and thermally conductive for establishing electric and thermal communication with said tissue;
ii) an electrical conductor connected to said tubular element so as to establish electrically conductive communication with said distal; and
iii) a cooling fluid passage within said tubular element and establishing fluid communication from a cooling fluid input at said proximal end of said tubular element to said distal end for establishing heat conductive communication therewith, and from said distal end to a cooling fluid output at said proximal end;

(b) providing a neutral plate in electrically conductive contact with said mammal;

(c) perforating said tissue with the distal end of said tubular element and penetrating said tubular element into said tissue;

(d) supplying electrical energy to said distal end of said tubular element through said conductor to effect tissue ablation proximate said distal end; and (e) while performing the step of supplying electrical energy, supplying cooling fluid to said distal end of said tubular element through said cooling fluid input and said cooling fluid passage so as to substantially prevent charring of said tissue and thereby to form a lesion of a specific volume within said tissue.

14. The method of claim 13, wherein said tissue comprises a tumor.

15. The method according to claims 13 or 14, wherein said electrical energy has a power in the range of 10 W to 70 W, with a frequency in the range of 10 KHz to 100,000 MHz.

* * * * *

UNITED STATES PATENT AND TRADEMARK OFFICE
CERTIFICATE OF CORRECTION

PATENT NO. : 5,951,546
DATED : September 14, 1999
INVENTOR(S) : Lorentzen

It is certified that error appears in the above-identified patent and that said Letters Patent is hereby corrected as shown below:

Title page, item [56] under U.S. DOCUMENTS, "4,961,535" should be --4,961,435--.

column 2, line 4, after "RF", insert --Tissue--.

Column 5, line 49, "spheric" should be --spherical--.

Column 5, line 52, after "diameter", "i" should be --in--.

Column 7, line 18, "promixal" should be --proximal--.

Column 7, line 36, "counter" should be --neutral--.

Column 13, line 12, "tract" should be --track--.

Signed and Sealed this

Sixth Day of June, 2000

Attest:

Q. TODD DICKINSON

*Attesting Officer*    Director of Patents and Trademarks